United States Patent
Hautvast

(10) Patent No.: US 9,691,159 B2
(45) Date of Patent: Jun. 27, 2017

(54) LOCAL CONTRACTION MEASUREMENTS

(71) Applicant: KONINKLIJKE PHILIPS N.V., Eindhoven (NL)

(72) Inventor: Guillaume Leopold Theodorus Frederik Hautvast, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/414,858

(22) PCT Filed: Jul. 3, 2013

(86) PCT No.: PCT/IB2013/055444
§ 371 (c)(1),
(2) Date: Jan. 14, 2015

(87) PCT Pub. No.: WO2014/013374
PCT Pub. Date: Jan. 23, 2014

(65) Prior Publication Data
US 2015/0213615 A1  Jul. 30, 2015

Related U.S. Application Data
(60) Provisional application No. 61/672,845, filed on Jul. 18, 2012.

(51) Int. Cl.
*G06K 9/00* (2006.01)
*G06T 7/20* (2017.01)
(Continued)

(52) U.S. Cl.
CPC ............ *G06T 7/20* (2013.01); *G01R 33/5608* (2013.01); *G01R 33/56308* (2013.01);
(Continued)

(58) Field of Classification Search
CPC .............. G01R 33/546; G01R 33/5608; G01R 33/56308; G06F 19/3431; G06F 19/3437;
(Continued)

(56) References Cited

U.S. PATENT DOCUMENTS 5,435,310 A     7/1995  Sheehan
6,917,826 B2 *  7/2005  Wei ....................... G06T 7/0012
                                                         128/898

(Continued)

FOREIGN PATENT DOCUMENTS

| | | |
|---|---|---|
| JP | 2004181041 A | 7/2004 |
| JP | 200587594 A | 4/2005 |
| WO | 2009089341 A1 | 7/2009 |

OTHER PUBLICATIONS

Sinusas, Albert J. et al "Quantification of 3-D Regional Myocardial Deformation: Shape-Based Analysis of Magnetic Resonance Images" American Journal Physiology Heart and Circulatory Physiology, vol. 281, 2001, pp. H698-H714.

(Continued)

*Primary Examiner* — Tom Y Lu

(57) ABSTRACT

A system (10) for quantification of uncertainty of contours includes a display (48) which displays a portion of a 4D image of at least a left ventricle over a plurality of cardiac phases. A measurement device (16) includes at least one processor (42) programmed to receive the 4D image (18) from an imaging device (12), receive a selected location on the myocardial wall of the left ventricle, cast a ray perpendicular to at least one of the myocardial wall or center of the left ventricle through the selected location, calculate a thickness the myocardial wall along the cast ray, evaluate myocardial wall motion over the range of the cardiac phases, calculate a quantification of the myocardial contractile func- (Continued)

tion, and display the calculate a quantification of the myocardial contractile function on the display device (48).

20 Claims, 3 Drawing Sheets

(51) Int. Cl.
    *G01R 33/56* (2006.01)
    *G01R 33/563* (2006.01)
    *G06F 19/00* (2011.01)
    *G06T 7/00* (2017.01)
    *G06T 15/06* (2011.01)
    *G01R 33/54* (2006.01)

(52) U.S. Cl.
    CPC ........ G06F 19/345 (2013.01); G06F 19/3431 (2013.01); G06F 19/3437 (2013.01); G06T 7/0016 (2013.01); G06T 15/06 (2013.01); G01R 33/546 (2013.01); G06T 2200/24 (2013.01); G06T 2207/10072 (2013.01); G06T 2207/10081 (2013.01); G06T 2207/10136 (2013.01); G06T 2207/20101 (2013.01); G06T 2207/30048 (2013.01); G06T 2210/41 (2013.01)

(58) Field of Classification Search
    CPC ... G06F 19/345; G06T 15/06; G06T 2200/24; G06T 2207/10072; G06T 2207/10081; G06T 2207/10136; G06T 2207/20101; G06T 2207/30048; G06T 2210/41; G06T 7/0016; G06T 7/20
    See application file for complete search history.

(56) References Cited

U.S. PATENT DOCUMENTS

| | | | |
|---|---|---|---|
| 7,308,297 | B2 | 12/2007 | Reddy |
| 7,974,694 | B2 | 7/2011 | Kramer |
| 8,096,947 | B2 * | 1/2012 | Salgo ................... A61B 8/0858 382/128 |
| 8,144,956 | B2 | 3/2012 | Salgo |
| 8,271,070 | B2 * | 9/2012 | Maier .................... A61B 5/055 382/173 |
| 2009/0131788 | A1 | 5/2009 | Settlemier |
| 2009/0136109 | A1 * | 5/2009 | Salgo ................... A61B 8/0858 382/131 |
| 2009/0148020 | A1 | 6/2009 | Sugiura |
| 2009/0161938 | A1 * | 6/2009 | Shekhar ............... A61B 8/0883 382/131 |
| 2009/0281415 | A1 | 11/2009 | Cupps |
| 2010/0022901 | A1 | 1/2010 | Breeuwer |

OTHER PUBLICATIONS

Hautvast, Gilion L.T.F. et al "Accurate Computer-Aided Quantification of Left Ventricular Parameters: Experience in 1555 Cardiac Magnetic Resonance Studies from the Framingham Heart Study", Magnetic Resonance in Medicine, 2011, pp. 1-9.

Petitjean, Caroline et al "A Review of Segmentation Methods in Short Axis Cardiac MR Images", Medican Image Analysis, 2011, pp. 1-16.

* cited by examiner

LOCAL CONTRACTION MEASUREMENTS

CROSS-REFERENCE TO PRIOR APPLICATIONS

This application is the U.S. National Phase application under 35 U.S.C. §371 of International Application No. PCT/IB2013/055444, filed on Jul. 3, 2013, which claims the benefit of U.S. Provisional Patent Application No. 61/672,845, filed on Jul. 18, 2012. These applications are hereby incorporated by reference herein.

The present application relates generally to image processing. It finds particular application in conjunction with the quantitative assessment of myocardial contractile function, especially, but not limited to, for quantification of wall thickening and wall motion from cardiac magnetic resonance (CMR), cardiac computed tomography (CCT), echocardiography, 3D ultrasound (3D US) image sequences. However, it is to be understood that it also finds application in other usage scenarios and is not necessarily limited to the aforementioned application.

Cine imaging using CMR, dynamic CCT, or 3D echocardiography enable quantification of global left ventricular (LV) function, including measurements of stroke volume, ejection fraction, and cardiac output. Cine imaging is also used to measure local contractile function, assessing the displacement of the endocardium (wall motion), or the thickening of the myocardium. As such, local contractile measurements are considered one of the standard diagnostic methods in the assessment of cardiac disease. In particular, local myocardial contractile function is a parameter for assessing myocardial salvage in relation to acute myocardial infarction, for assessing myocardial dyssynchrony for planning CRT procedures, and for assessing stress induced wall motion abnormalities in pharmacologically induced stress testing.

To measure global LV function or local contractile function, cine images of the heart are delineated or segmented. In addition to the manual delineation of all images (multiple slices and phases), many semi-automatic and automatic contour detection methods have been developed, and are available in several dedicated functional analysis packages. However, despite the availability of automatic contour detection methods, complete and correct delineation of the myocardial contours in multiple slices and phases is time consuming. For example, automatic contour detection methods do not provide error free data sets, but rather require the contours to be reviewed and manually corrected. This review and correction of the myocardial contours at all slices usually takes between 3 and 5 minutes, but may take up to 10 minutes, depending on image quality, algorithm accuracy, number of slices, and application usability. Consequently, many routine users are still dissatisfied with the time efficiency of the delineation tools and LV functional analysis as a whole.

In addition, such a full analysis results in measurements of local contractile function for all myocardium locations, commonly reported in bulls-eye views as shown in FIG. 1. The bulls-eye views 2 illustrate a quantification of the local contractile function. Specifically, the bulls-eye view indicates the time dispersion 4 of contractility 6 for each of various LV segments. However, such cardiac imaging reporting standards prescribe documentation of local contractile function in a high number of locations. Furthermore, local wall motion abnormalities are often rapidly recognized during visual inspection, such that complete analysis for the sole purpose of documentation of the local abnormality is perceived as an unnecessary activity.

The present application provides new and improved methods and systems which overcome the above-referenced challenges and others.

In accordance with one aspect, a system for quantification of myocardial contractile function is provided. The system including at least one processor programmed to receive an image including an object of interest, receive a selected position from a user on a portion of the received image, determine a quantification of myocardial contractile function at the selected position, and display the quantification of myocardial contractile function on a display device.

In accordance with another aspect, a method for quantification of myocardial contractile function is provided. The method including receiving an image including an object of interest, receiving a selected position from a user on a portion of the received image, determining a quantification of myocardial contractile function at the selected position, and displaying the quantification of myocardial contractile function on a display device.

In accordance with another aspect, a system for quantification of uncertainty of contours is provided. The system including a display which displays a portion of a 4D image of at least a left ventricle over a plurality of cardiac phases. A measurement device includes at least one processor programmed to receive the 4D image from an imaging device, receive a selected location on the myocardial wall of the left ventricle, cast a ray perpendicular to at least one of the myocardial wall or center of the left ventricle through the selected location, calculate a thickness the myocardial wall along the cast ray, and display the thickness of myocardial wall on the display device.

One advantage resides in time efficient analysis of local contractile function.

Another advantage resides in the quantification of local contractile function at user selected locations.

Another advantage resides in detailed reporting and documentation of local contractile function.

Another advantage resides in increased patient throughput.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Typically, when assessing myocardial contractile function, one of the key measurements to quantify is the wall thickness and the wall motion of the LV. Currently, a series of slice images, typically at least 10, are taken in each of a plurality of cardiac phases, typically at least a dozen phases. These images are then segmented, particularly, the inner and outer walls of the LV. Even with automatic segmentation techniques, the user normally spends at least a couple of minutes per slice image adjusting the segmentation which causes this process to be very time consuming.

Figure 2:
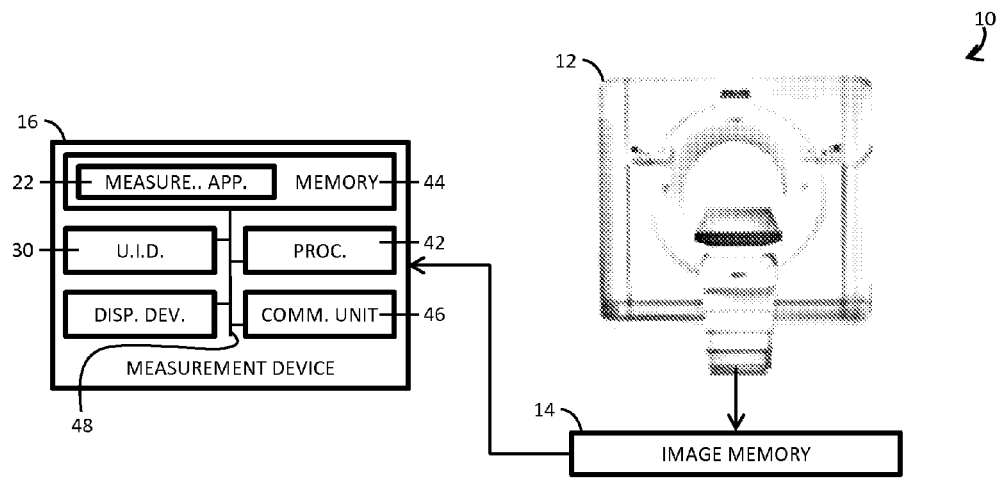
FIG. 2 illustrates a block diagram of a system for measuring local contraction in accordance with the present application.

With reference to FIG. 2, a therapy system 10 provides a quantitative assessment of myocardial contractile function, especially, but not limited to, for quantification of wall thickening and wall motion from cardiac magnetic resonance (CMR), cardiac computed tomography (CCT), echocardiography, 3D ultrasound (3D US) imaging sequences. Specifically, a local contractile function is quantified at a location indicated by a user. When the user indicates a location at the myocardium in a pilot image, the therapy system 10 does not require the radiologist to verify and/or correct a full left ventricular (LV) segmentation for the mere purpose of documenting a visually confirmed wall motion abnormality. Instead, a single interaction enables documentation of the wall motion and the wall thickness at the indicated location. As such, the workflow enables time efficient analysis of local contractile function, without unnecessary overhead.

The therapy system 10 includes one or more imaging modalities 12 for acquiring images of objects of interest, such as a myocardium, within patients. The imaging modalities 12 suitably include one or more of a computed tomography (CT) scanner, a CMR scanner, a cardiac computed tomography CCT scanner, a echocardiography scanner, a 3D US scanner, and the like. Images acquired from the imaging modalities 12 are stored in one or more image memories 14.

Figure 3:
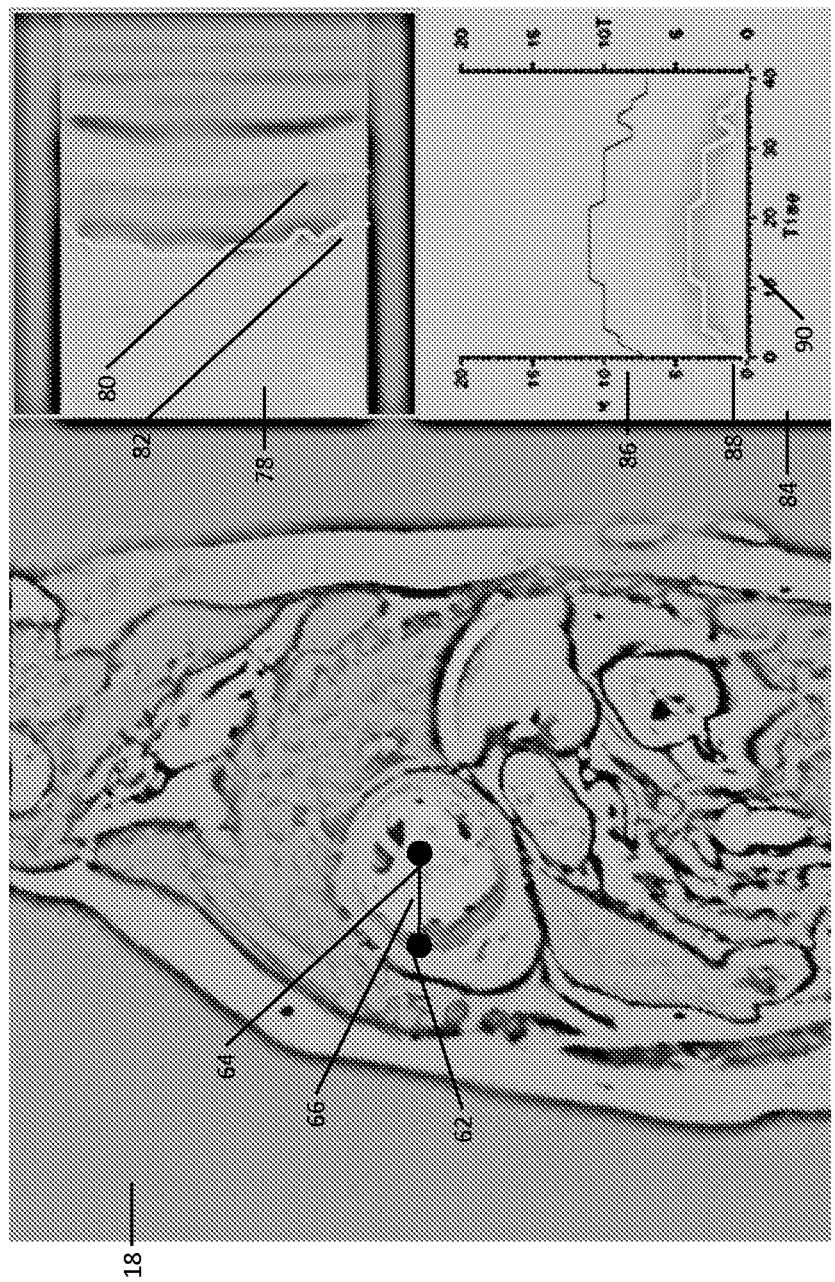
FIG. 3 illustrates an exemplary embodiment of the user interface in accordance with the present application.

A measurement device 16 receives an image 18, such as a two-, three- and/or four-dimensional image, of an object of interest (OOI) 20, such as a myocardial, an example of which is shown in FIG. 3. In one embodiment, the image is a 4D image, such as a 3D cine image of the heart. The received image 18 can, for example, be a Dynamic Contrast Enhanced MR image, a CT image, CMR image, a CCT image, a 3D US image, and the like. Typically, the image 18 is received from the imaging modalities 12 and/or the image memories 14. For example, the image 18 can be received from the imaging modalities 12 through the image memories 14. However, other sources for the image 18 are contemplated. Further, the image 18 is typically received from magnetic resonance and/or computed tomography imaging modalities. Through execution of a measurement application 22 of the measurement device 16, the measurement device 16 assesses the myocardial contractile function of the receive image 16. The exemplary embodiment focuses on the analysis of local myocardial contractile function from cine CMR data, however, the workflow is also applicable to cine images from other modalities (CCT, Echocardiography, etc.). In addition, the exemplary embodiment utilizes a combination of algorithms that are suitable for the analysis of short-axis (SA) cine CMR data, whereas the exemplary embodiment is not limited to that particular combination. For example, all algorithms are 2D, but can be extended to similar concepts in 3D for application to CCT or 3D US.

When the measurement application 22 is executed, a user interface thereof is displayed on a display device 24 of the measurement device 16. The user interface suitably allows an associated user to view the received image 18, e.g. slice images in a selected cardiac phase. Further, the user interface allows the associated user to select a location on the received image 18 at which a local contractile function is to be quantified using a user input device 30 of the of the measurement device 16. In response to receiving the location on the received image 18, the measurement device 16, such as with the measurement application 22, generates quantitative parameters of contractile function at that location. Hence, the associated user can, for example, employ a mouse to indicate a location on the displayed image 18 to determine a quantification of local contractile function at an indicated location. In some embodiments, the user interface further allows the associated user to specify other parameters for measurement using the user input device 30. For example, the measurement application 22 enables the user to view the images for suspicious areas. The user utilizes the user input device 30 to select the suspicious area/point and the measurement device 16 automatically measures the thickness of the LV wall at that point. The thickness of the LV wall is then displayed as a number or other quantity on the display device 24. It is also contemplated that a graph depicting changes in wall thickness and/or displacement is also displayed on the display device 24.

The measurement device 16 does not require the user to verify and/or correct a full left ventricle (LV) segmentation for the mere purpose of documenting a visually confirmed wall motion abnormality. Instead, a single interaction enables documentation of the wall motion abnormality at the desired location. As such, the measurement device 16 enables time efficient analysis of local contractile function, without unnecessary overhead.

Figure 4:
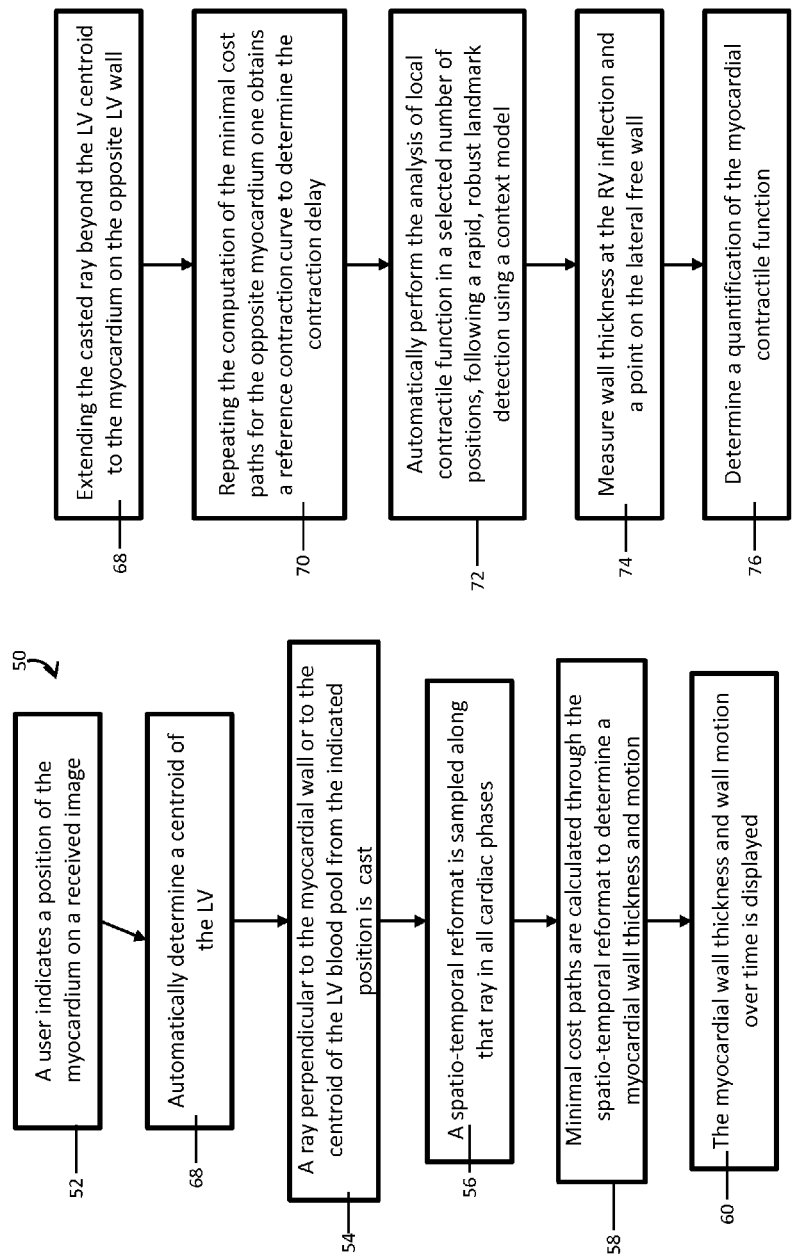
FIG. 4 illustrates a block diagram of a method for measuring local contraction in accordance with the present application.

To quantify a local contractile function, the measurement device 16 employs a method of FIG. 4. According to the method 50, a user indicates a position of the myocardium on a received image in a step 52. In a step 54, a ray perpendicular to the myocardial wall or to the centroid of the LV blood pool from the indicated position is cast through the selected location. A spatio-temporal reformat is sampled along that ray in all cardiac phases in a step 56. In a step 58, minimal cost paths are calculated through the spatio-temporal reformat to determine a myocardial wall thickness and motion. The myocardial wall thickness and wall motion over time is displayed in a step 60.

Referring to FIG. 3, after the user selects a position 62 of the myocardium on the received image 18 in a step 52, the measurement device 16 automatically determines a centroid 64 of the LV and draws a line 66 from the centroid 64 through the selected point in 62 in a step 52 order to assure that the line 66 is perpendicular to the LV wall. To accomplish this, the measurement application 22 utilizes a best fitting circle of the LV to determine the most accurate location of the centroid 64. Thus, the line is positioned at the same distance as the radius between the centroid and the LV wall. After the line 64 is drawn from the centroid 64 through the selected point 62 in a step 56, one or more transition points are determined between the blood pool and the LV wall through the various cardiac phases. For example, a tracking algorithm or location tracking is utilized to determine the location of the selected point 62 and the centroid 64 through the cardiac phases of the 3D cine images. The transition points between the blood pool and the LV wall and the outside of the heart wall of the LV are determined automatically and the distance between them automatically calculated in a step 58. The distances through the various cardiac phases are stored and utilized to determine the quantification of the myocardial contractile function. The location of the selected point (inner LV wall, exterior wall, center point of wall, etc.) in the cine images and a maximum LV displacement, e.g. relative to the centroid, LV min displacement, wall motion, etc. is determined. The quantification of myocardial contractile function includes the LV wall thickness, the LV maximum displacement, the LV minimum displacement, the wall motion, and the like. In this manner, a fully automated assessment of myocardial contractile function is performed. It is also contemplated that the measurement points are selected automatically. For example, the thickness of the end wall is measured at the two end points of the RV, at a point in between, such as on the level of the middle of the ventricular septum, and at a point in the lateral free wall (across the blood pool from the middle of the LV septum).

It should also be contemplated that the exemplary embodiment of FIGS. 3 and 4 can be adapted to allow for local dyssynchrony assessment, by extending the casted ray beyond the LV centroid to the myocardium on the opposite LV wall in a step 68. By repeating the computation of the minimal cost paths for the opposite myocardium one obtains a reference contraction curve, that is used in a step 70 to determine the contraction delay between e.g. the septum and the free lateral wall. Furthermore, the implementation in FIGS. 3 and 4 can also be adapted to automatically perform the analysis of local contractile function in a selected number of positions, following a rapid, robust landmark detection using a context model in a step 72. For example, two T-junctions with the same distance to a center point can be utilized to identify the RV inflections. Together, these points can be used to measure wall thickness at the RV inflection and a point on the lateral free wall in a step 74.

Figure 1:
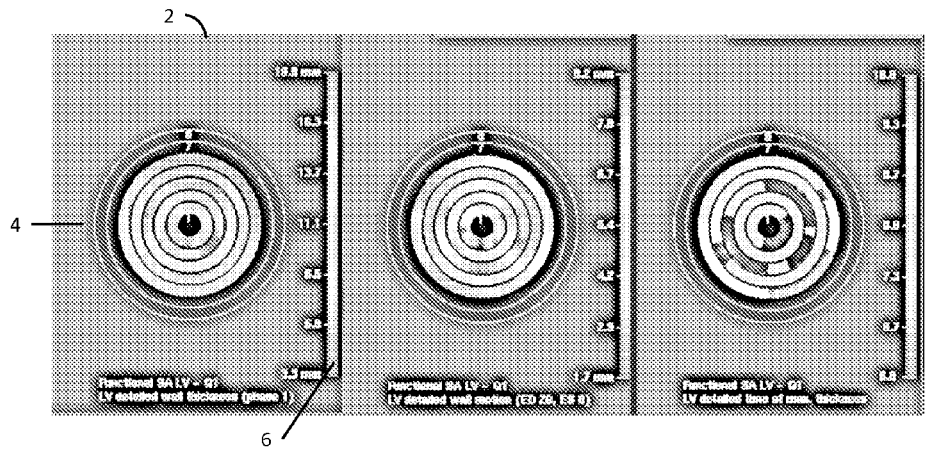
FIG. 1 illustrates conventional bulls-eye views in accordance with the present application.

After the quantification of the myocardial contractile function is determined, the measurement device 16 in a step 76 displays the quantification. In one embodiment, the quantification is displayed in conventional bulls-eye views as shown in FIG. 1. In another embodiment, the quantification is displayed graphically as shown on the right side of FIG. 3. In a top graph 78, the quantification displays a wall thickness of the myocardial. Two indicators 80, 82 display the inner and outer wall of the myocardial. The bottom graph 84 displays a maximum 86 and minimum 88 displacements of the myocardial over time 90. It is also contemplated that the quantification of the myocardial contractile is displayed as a numerical value shows on the displayed image 18. It should be appreciated as the user selects various points or areas on the displayed image 18, the measurement device 16 display one or more indicators of the quantification of the myocardial contractile function.

The measurement device 16 includes at least one processor 42 executing computer executable instructions on at least one memory 44 thereof. The computer executable instructions carry out the functionality of the measurement device 16 and include the measurement application 22. In one embodiment, the processor is programmed to perform the steps described in conjunction with FIG. 4. Further, the measurement device 16 can include a communication unit 46 and/or at least one system bus 48. The communications unit 46 provides the processor 42 with an interface to at least one communication network. The communications unit 46 can, for example, be employed to communicate with the imaging modalities 12 and/or the image memories 14. The system bus 48 allows the exchange of data between the display device 24, the user input device 30, the processor 42, the memory 44 and the communication unit 46.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a user input device includes one or more of a mouse, a keyboard, a touch screen display, one or more buttons, one or more switches, one or more toggles, and the like; a database includes one or more memories; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A system for quantification of myocardial contractile function, said system comprising:
at least one processor programmed to:
receive a 4D image including a series of 3D images over time of a left ventricle over a plurality of cardiac phases;
receive a selected position on a surface of a myocardial wall of the left ventricle in the image from a user interface;
determine a thickness of the myocardial wall at the selected position, without a complete delineation of a surface of the myocardial wall; and
control a display device to display a function of the determined thickness.

2. The system according to claim 1, wherein the at least one processor is further programmed to:
determine a quantification of a myocardial contractile function based on the determined thickness over the plurality of cardiac phases and control the display device to display the quantification of the myocardial contractile function.

3. The system according to claim 1, wherein the at least one processor is further programmed to determine the thickness of the myocardial wall at the selected location by:
casting a ray perpendicular to at least one of the myocardial wall or center of the left ventricle from the selected position; and
determine a distance along the ray between a blood pool in the left ventricle and the surface of the myocardial wall, the determined distance along the ray being indicative of the thickness of the myocardial wall.

4. The system according to claim 1, wherein the at least one processor is further programmed to:
repeatedly measure the distance along the ray between the blood pool and the surface of the myocardial wall over the plurality of cardiac phases;
repeatedly measure motion of the myocardial wall over the plurality of cardiac phases; and
calculate a myocardial contractile function based on the measured distances and the measured motion over the plurality of cardiac phases.

5. The system according to claim 1, further including:
an imaging apparatus which generates the 4D image; and
an user input device which provides the selected position from the user to the at least one processor.

6. The system according to claim 1, wherein the at least one processor is programmed to determine the thickness by:
determining a centroid of the left ventricle;
drawing a line between the centroid and the selected position;
determining a transition point along the line between a blood pool of the left ventricle and the myocardial wall.

7. A method for quantification of a myocardial contractile function, said method comprising:
receiving a series of 3D images including left ventricle, the left ventricle including a myocardial wall;
receiving a selected position on the myocardial wall;
casting a ray from the selected position perpendicular to and through the myocardial wall;
determining a thickness of the myocardial wall along the ray in each of the series of 3D images;
determining displacements of the myocardial wall over the series of images;
determining a quantification of a myocardial contractile function at the selected position based on the determined thicknesses and displacements; and
displaying the quantification of the myocardial contractile function on a display device.

8. The method according to claim 7, wherein determining the thickness of the myocardial wall includes determining transition points (a) between a blood pool and the myocardial wall and (b) at an outside of the myocardial wall over the series of 3D images.

9. The method according to claim 7, wherein determining the displacement includes determining left ventricle maximum displacement, left ventricle minimum displacement, and left ventricle wall motion.

10. The method according to claim 7, wherein determining the quantification of the myocardial contraction function includes:
calculating minimal cost paths over the series of 3D images.

11. The method according to claim 7, wherein casting the ray includes:
determining a centroid of the left ventricle;
casting the ray between the centroid and the selected position.

12. At least one processor programmed to perform the method according to claim 7.

13. A non-transitory computer readable medium carrying software which controls one or more processors to perform the method according to claim 7.

14. A system for quantifying a myocardial contractile function, the system comprising:
one or more processors configured to:
receive a series of 3D images of at least a left ventricle over a plurality of cardiac phases,
receive a location on a myocardial wall of the left ventricle,
cast a ray intersecting the received location and the myocardial wall, the ray being cast perpendicular to the myocardial wall,
determine thicknesses of the myocardial wall along the ray over the plurality of cardiac phases,
determine movement of the myocardial wall over the plurality of cardiac phases,
determine the myocardial contractile function using the determined movement and thicknesses at the received location, and
controlling a display to display at least one of the myocardial contractile function, portions of the series of 3D images, the determined thickness and the determined motion over time.

15. The system according to claim 14, wherein the one or more processors are further configured to:
determine left ventricle maximum displacement and left ventricle minimum displacement over the plurality of cardiac phases; and
wherein the myocardial contractile function is determined using the left ventricle maximum displacement, the left ventricle minimum displacement, and the determined movement of the myocardial wall.

16. The system according to claim 14, wherein the one or more processors are configured to determine the thickness of the myocardial wall along the ray by:
determining transition points along the ray indicative of (a) an outside of the myocardial wall and (b) an interface between a blood pool and the myocardial wall.

17. The system according to claim 14, further including:
a user interface configured to enable a user to manually select the location on the myocardial wall.

18. The apparatus according to claim 17, further including:
a display device which is controlled by the one or more processors to display at least one of the myocardial contractile function, portions of a series of 3D images, the graph of the determined thickness, and the graph of the determined motion.

19. A system for quantification of myocardial contractile function of an object of interest, said system comprising:
at least one processor programmed to:
receive an image including the object of interest;
receive a selected position from a user on a portion of the received image at which the myocardial contractile function is to be quantified;
determine a quantification of a myocardial contractile function at the selected position without segmentation and a complete delineation of surfaces of interest of the object; and
display the quantification of myocardial contractile function on a display device.

20. The system according to claim 19, wherein the object of interest is a left ventricle of a patient and the surfaces of interest are surfaces of the myocardial wall of the left ventricle.

* * * * *